United States Patent
Cho

(10) Patent No.: US 6,913,025 B2
(45) Date of Patent: Jul. 5, 2005

(54) CALLUS-REMOVING SKIN-FILE AND METHOD OF MANUFACTURING THE SAME

(76) Inventor: In-sool Cho, 101-1604 Hanra Dongbaek Apt., 565 Ssangyong 1-dong, Cheonan-shi, Chungcheongnam-do (KR)

( * ) Notice: Subject to any disclaimer, the term of this patent is extended or adjusted under 35 U.S.C. 154(b) by 213 days.

(21) Appl. No.: 10/372,535

(22) Filed: Feb. 24, 2003

(65) Prior Publication Data

US 2003/0172945 A1 Sep. 18, 2003

(30) Foreign Application Priority Data

Mar. 12, 2002 (KR) ................................ 10-2002-0013282
Oct. 9, 2002 (KR) ................................ 20-2002-0030113

(51) Int. Cl.$^7$ .................... A45D 29/18; A45D 24/00
(52) U.S. Cl. .................... 132/76.4; 132/75.6; 132/200
(58) Field of Search .................... 132/76.4, 75.6, 132/200, 73.5

(56) References Cited

U.S. PATENT DOCUMENTS 4,422,465 A * 12/1983 Haga ........................ 132/76.4
5,119,839 A * 6/1992 Rudolph .................... 132/200
2002/0066459 A 6/1902 Turina

FOREIGN PATENT DOCUMENTS

EP 1138221 10/2001
WO WO 0066324 11/2000

* cited by examiner

*Primary Examiner*—John J. Wilson
*Assistant Examiner*—Robyn Kieu Doan
(74) *Attorney, Agent, or Firm*—John P. White; Cooper & Dunham LLP

(57) ABSTRACT

The present invention relates to a callus-removing skin-file capable of removing fingernails, toenails, calluses and the like and a method of manufacturing the same. The callus removing file 21, comprises a base plate 24 made of glass, an abrasive layer 23 formed on the base plate by sanding; and a coating layer 22 coated on the upper surface of the abrasive layer 23 with a mixture of epoxy resin, a hardening agent and emery. The method of manufacturing the callus-removing skin-file includes the steps of: preparing a base plate 24 made from glass material; making a mixture by mixing 20 to 25 percent by weight epoxy resin, a 40 to 55 percent by weight hardening agent and 15 to 20 percent by weight emery; forming an abrasive layer 23 by sanding a surface of the base plate 24; coating the mixture on the upper surface of the sanded base plate; and hardening the base plate 24 coated with the mixture.

8 Claims, 5 Drawing Sheets

CALLUS-REMOVING SKIN-FILE AND METHOD OF MANUFACTURING THE SAME

BACKGROUND OF THE INVENTION

1. Field of the Invention

The present invention relates to a file, more particularly to a callus-removing skin-file and a method of manufacturing the same.

2. Description of the Related Art

At the site of repeated pressure and friction, such as the hands, feet and knees of one's body, the skin easily builds up to form thick layers of calloused skin.

If such layers of calluses are not removed, that portion becomes dry and rough, and the skin gets hardened and cracked. This may produce pain, with the result that the aesthetic appearance is spoiled.

Thus, calluses have been conventionally removed by rubbing the rough bottom surface of the bathhouse against the calluses, using a stone during bathing, or by cutting the calluses off with a knife or the like. However, when removing calluses by a stone, it is inconvenient to carry the stone because it is heavy. Moreover, the method of cutting calluses by knife generates problems such as pain caused by damage to the healthy skin not the calluses.

To overcome these problems, a file for rubbing calluses was proposed. However, for conventional files, thick ceramic powder or stone dust are only stacked on the surface of the file, so the ceramic power or stone dust is gradually removed over time, thus disabling their functions and resulting in a short life span.

An abrading tool for callus removal was disclosed in European Patent Application No. 01104902.0 (Laid-Open No. EP 1 138 221 A1). In the European Patent Application, a surface becomes roughened by use of sanding or acid-engraving on flat, pressed or hardened glass. Such a method has problems in that the roughness is not maintained for time use.

In order to overcome the above-mentioned problem, a nail file using sanding was disclosed and has been used. FIG. 1 is a perspective view of a conventional glass nail file. As shown therein, the conventional nail file 11 includes a glass layer 13 which is formed in a flat bar shape so that it can be easily held, an abrasive layer 12 formed on an upper surface of the glass layer 13 for abrading nails and the like and a handle portion 14 at one end of the glass layer 13 on which the abrasive layer 12 is not formed and which is hand-held by a user.

In the nail file 11, after carrying out a pre-sanding operation by masking the remaining portion except the portion where the abrasive layer 12 is to be formed on the glass layer 13 using a masking tape, sanding treatment is performed on the portion where the abrasive layer 12 of the glass layer 13 is to be formed.

However, the above-mentioned nail file has a problem in that the roughness of the abrasive layer becomes smooth after repeated use as a result of the characteristics of glass, thereby shortening the life span of the nail file.

Additionally, since the nail file is made of glass material, if it is dropped or a strong force is applied thereto, the nail file may break generating broken pieces of glass. This means that a risk of accident always exists.

SUMMARY OF THE INVENTION

Therefore, it is an object of the present invention to provide a callus-removing skin-file that removes calluses by contacting with callused areas and a method of manufacturing the same, which can be used for a long time maintaining a certain roughness on the entire abrasive layer and which can be easily manufactured at a low cost.

To achieve the above object, there is provided a callus-removing skin-file comprising: a base plate made of glass; an abrasive layer formed on the base plate by sanding; and a coating layer coated on the upper surface of the abrasive layer with a mixture of epoxy resin, a hardening agent and emery.

Preferably, the amount of epoxy resin is 20 to 25 percent by weight, the amount of the hardening agent is 40 to 55 percent by weight, and the amount of the emery is 15 to 20 percent by weight.

Preferably, the callus-removing skin-file may further comprise a protective layer formed on the back surface of the base plate which prevents the spread of pieces of glass upon the breakage of the base plate.

Preferably, the callus-removing skin-file may also include a brush formed on the back surface of the base plate which brushes up calluses.

In addition, a handle portion forms on at least one part of the base plate to which various kinds of advertisements are attachable. A groove forms on at least one part of the base plate to which a mirror is attachable.

In accordance with another aspect of the present invention, there is also provided a method of manufacturing a callus-removing skin-file comprising the steps of: preparing a base plate made from glass material; making a mixture by mixing 20 to 25 percent by weight epoxy resin, a 40 to 55 percent by weight hardening agent and 15 to 20 percent by weight emery; forming an abrasive layer by sanding a surface of the base plate; coating the mixture on the upper surface of the sanded base plate; and hardening the base plate coated with the mixture.

Preferably, the glass material is one selected from plate glass, press glass, flat glass, colored glass and specific glass such as water glass, ripple glass, etc.

BRIEF DESCRIPTION OF THE DRAWINGS

The above objects, features and advantages of the present invention will become more apparent from the following detailed description when taken in conjunction with the accompanying drawings, in which.

DETAILED DESCRIPTION OF THE PREFERRED EMBODIMENT

A preferred embodiment of the present invention will now be described with reference to the accompanying FIG. 2.

Figure 1:
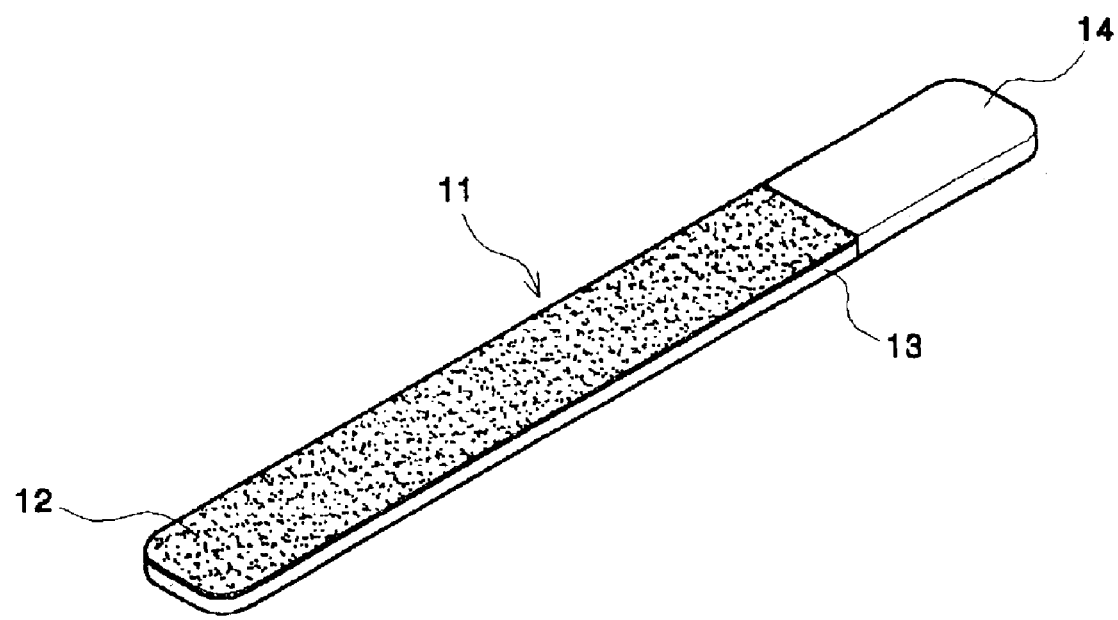
FIG. 1 is a perspective view of a conventional glass nail file.
Figure 2:
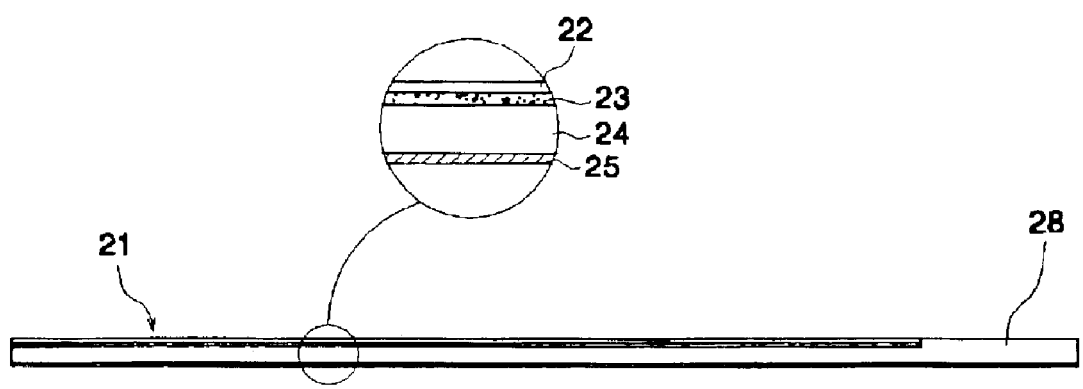
FIG. 2 is a side sectional view of a callus-removing skin-file in accordance with an embodiment of the present invention.

FIG. 2 is a side sectional view of a callus-removing skin-file according to an embodiment of the present invention.

The callus-removing skin-file includes a base plate 24, an abrasive layer 23 and a coating layer 22.

The base plate 24 is made of glass material such as plate glass, press glass, flat glass, colored glass and specific glass (water glass, ripple glass, etc.). The abrasive layer 23 is formed on the base plate 24 by sanding.

The coating layer 22 is coated on the upper surface of the abrasive layer 23 with a mixture of epoxy resin, a hardening agent (for example, polyamide resin) and emery at a predetermined mixing ratio thereby hardening the resulting mixture. At this time, the epoxy resin is mixed with the hardening agent, i.e., polyamide resin, to thus bond the materials with a high strength. The emery forms a rough surface, serves as an abrasive material, and is applied to callus areas to thereby remove the calluses.

At this time, if the content of the epoxy resin as a bonding agent, and the content of the polyamide resin as a hardening agent, are too excessive with respect to the entire mixture of the file, the materials become soft, and thus they cannot perform their functions for removing calluses even after the file mixture is hardened. Hence, a 20 to 25 percent by weight epoxy resin, a 40 to 55 percent by weight hardening agent and a 15 to 20 percent by weight emery are mixed, so that the obtained mixture can form an abrasive enough surface to remove calluses when hardened.

A method of manufacturing a callus-removing skin-file according to the present invention will now be described. The manufacturing method includes the steps of: preparing a base plate 24 made from glass material; making a mixture, by mixing 20 to 25 percent by weight epoxy resin, a 40 to 55 percent by weight hardening agent and 15 to 20 percent by weight emery; forming an abrasive layer 23 by sanding a surface of the base plate 24; coating the mixture on the upper surface of the sanded base plate; and hardening the base plate 24 coated with the mixture.

In the step of preparing the base plate 24, the glass material is one of selected from plate glass, press glass, flat glass, colored glass and specific glass such as water glass, ripple glass, etc.

In the step of making a mixture, 20 to 25 percent by weight epoxy resin, a 40 to 55 percent by weight hardening agent and 15 to 20 percent by weight emery are mixed.

The abrasive layer 23 is formed by processing the base plate 24 made from the glass material so as to have a rough surface by rubbing the surface of glass with air and a rubbing stone, i.e., sanding processing, in order to maximize a surface roughness.

In addition, the base plate 24 can be provided with a handle portion 28 to which various kinds of advertisements are attachable when it is formed. At the back surface of the base plate 24, there is additionally formed a protective layer 25 for preventing pieces of glass from splintering upon damage of the base plate 24. The protective layer 25 can be made from plastic, metal, wood and the like.

In the coating step, the mixture of epoxy resin, polyamide resin as a hardening agent and emery is coated on the upper surface of the abrasive layer 23.

In the hardening step, by hardening the coating, the callus-removing skin-file suitable for callus removal according to the present invention is manufactured. The surface area of the file contacted with callus areas is formed rougher. For this, in the step of hardening the file mixture, an abrasive material, i.e., emery, is additionally applied to the surface of the file mixture before the mixture is completely hardened, so that the surface area can be formed rougher to thus remove calluses easily while maximizing abrasive force when rubbing the calloused area. For the emery, a sufficient effect can be obtained by applying a 1 to 5 percent by weight emery with respect to the entire mixture.

As described above, applying emery in the step of hardening the file mixture, the surface area of the file becomes rougher thereby maximizing abrasive force and increasing a callus removing effect. Additionally, the file mixture contains an amount of abrasive material, i.e., emery, allowing enough roughness required for callus removal even though the emery applied on the surface area is stripped off when the file is used for a long period. Thus, there is no limitation in further use of the callus removing file, so the life span of the file is lengthened.

In the step of manufacturing the callus-removing skin-file after hardening the mixture, the obtained mixture is put in a mold having a predetermined shape and then hardened so that various types of files can be manufactured.

Other embodiments of the present invention will now be described. In the following embodiments, the same drawing reference numerals are used for the same elements through FIGS. 3 to 5, as compared with the above-mentioned embodiment of FIG. 2.

Figure 3:
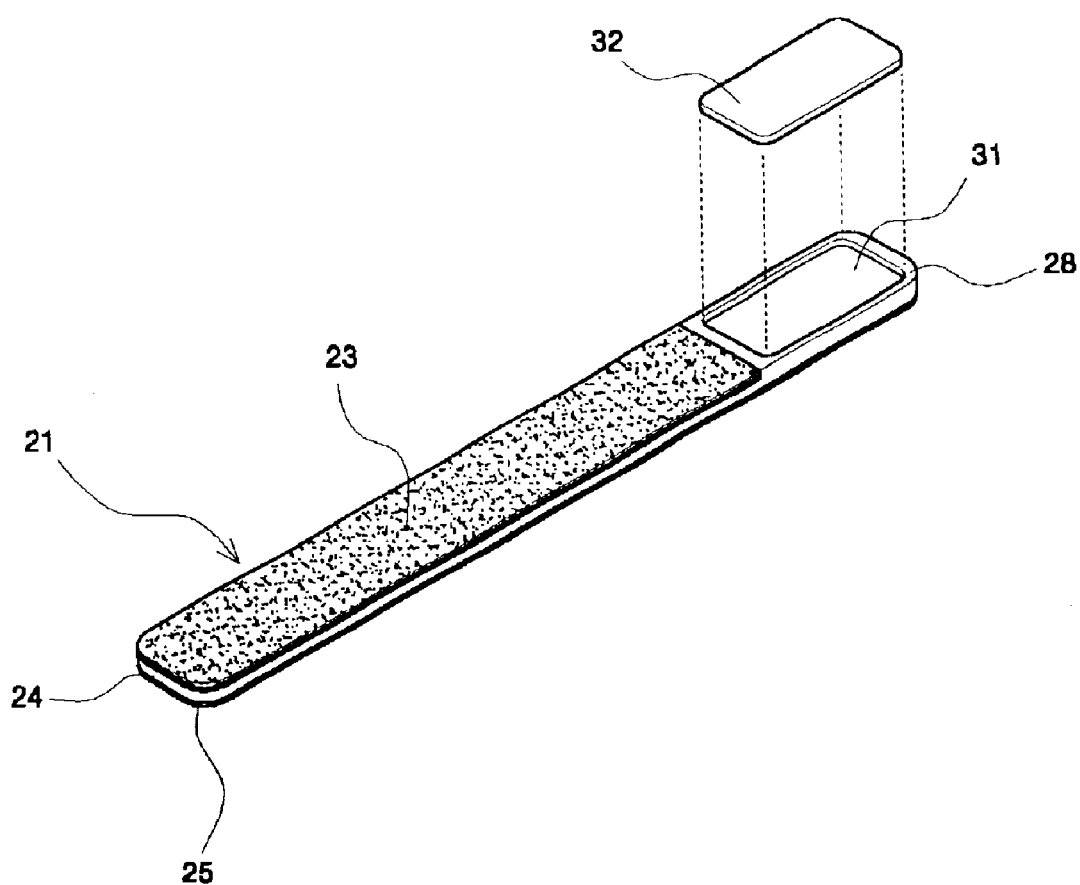
FIG. 3 is a decomposed perspective view showing a callus-removing skin-file with a mirror attached to a handle portion thereof in accordance with another embodiment of the present invention.
Figure 4:
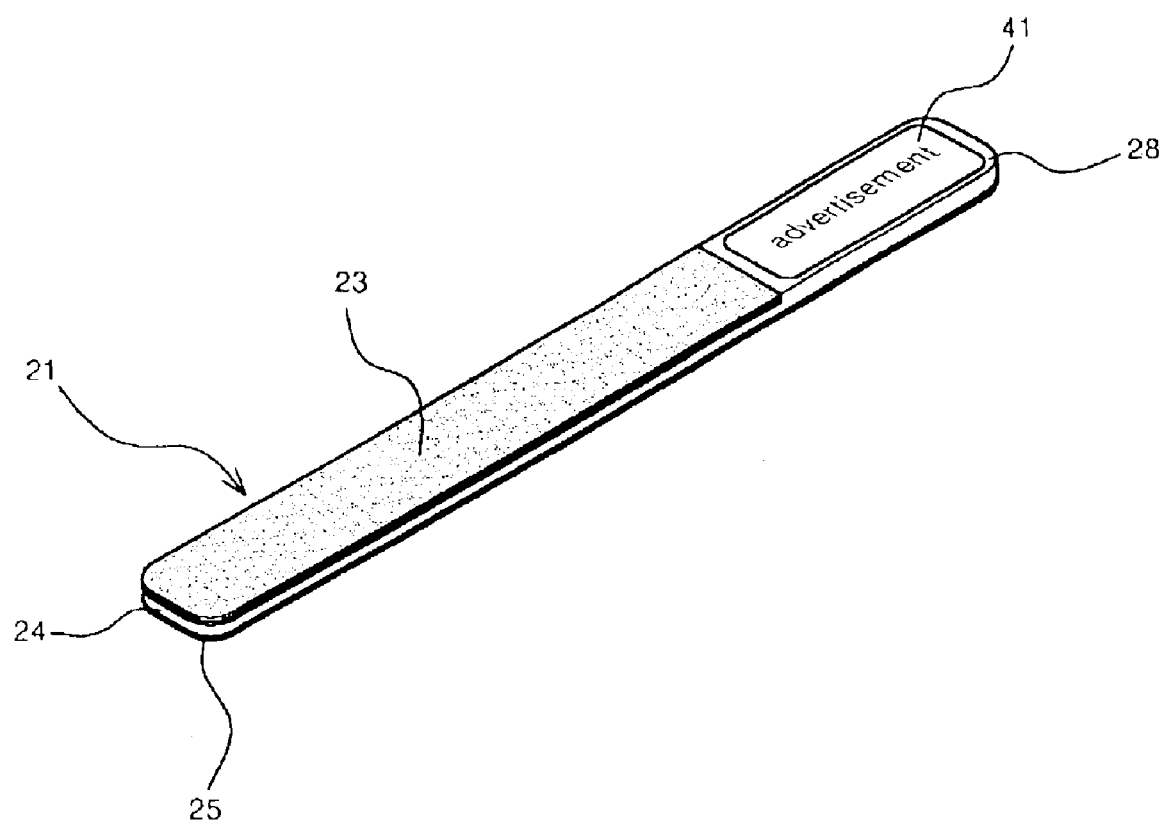
FIG. 4 is a perspective view showing a callus-removing skin-file having an advertisement attached to the handle portion thereof in accordance with still another embodiment of the present invention.
Figure 5:
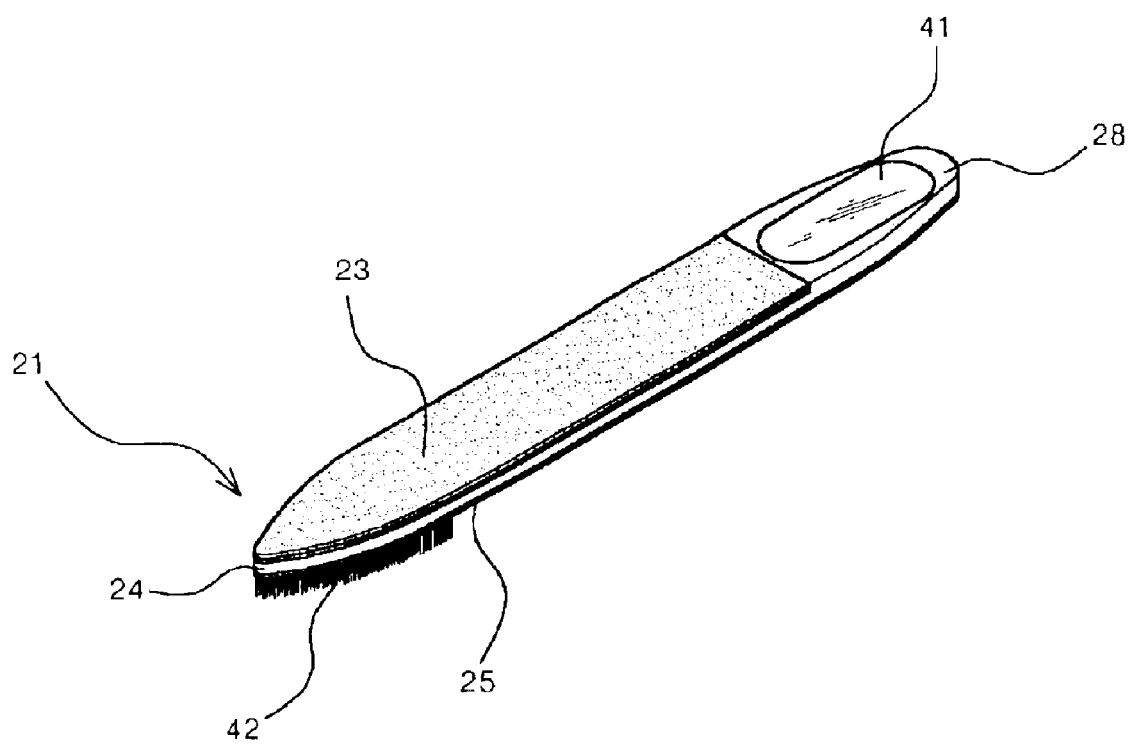
FIG. 5 is a perspective view showing a callus-removing skin-file with a brush attached to the back surface thereof in accordance with yet another embodiment of the present invention.

FIGS. 3 to 5 are perspective views of the callus-removing skin-file according to other embodiments of the present invention, respectively.

Firstly, as shown in FIG. 3, there is provided a callus-removing skin-file 21 having a mirror 32 being attached to the handle portion 31 thereof in accordance with another embodiment of the present invention. For receiving the mirror 32, a groove 31 is formed at one side of the handle portion 28 and the mirror 32 can be inserted and coupled to the groove 31.

Second, as show in FIG. 4, there is provided a callus-removing skin-file 21 having an advertisement 41 attached to the handle portion 28 thereof in accordance with still another embodiment of the present invention. In accordance with this embodiment, it is possible to attach the advertisement 41 printed with various kinds of ad copies or patterns on one side of the handle portion 28. The advertisement 41 can be attached by direct printing, decalcomania, sticker, sanding engraving and the like.

Third, as shown in FIG. 5, there is provided a callus-removing skin-file having a brush 42 attached to the back surface thereof in accordance with yet another embodiment of the present invention. The brush 42 for brushing up calluses can be selectively provided at the back surface of the base plate 24 or protective layer 25.

Although the callus-removing skin-file according to the present invention can be applied to separate tools of various shapes, it also can be used alone for the use of callus removal, which is no more than an option of the manufacturer.

Moreover, the callus-removing skin-file of the present invention can be used differently according to extent of calluses, age group, target application area and purpose. This can be achieved by differentiating the grain size of the abrasive material, i.e., emery in the file mixture.

If the grain size of the abrasive material in the mixture is too small, the skin may be wounded. In contrast, if too large, a desirable callus removal effect cannot be attained. Therefore, it is preferable that the grain size of the abrasive material, i.e., emery, is within the range of 50 to 3000 meshes. The grain size of 50 to 150 meshes is used for removing calluses of the feet, the grain size of 150 to 500 meshes is used for abrading nails, and the grain size of 500 to 3000 meshes is used for polishing fingernails and toenails.

In this way, in the callus-removing skin-file and the method of manufacturing the same according to the present invention, the file is easy to manufacture and an advertisement is freely attachable thereto, so it is of high utility value in advertising articles. Additionally, since it has a brush and mirror attached thereto, it is easily used in every cosmetic purpose for people and pets, thereby maximizing effectiveness in its use.

As described above, in the callus-removing skin-file and the method of manufacturing the same according to the present invention, the file is made by hardening the mixture of epoxy resin, a hardening agent and emery, so its manufacturing process is simple and the manufacturing cost is low. Also, since the file maintains a certain roughness over the entire thickness of the abrasive layer, it can be used continuously even though a part of the surface is worn out or stripped off due to its long time use, thereby lengthening the life span. Moreover, if an abrasive material is applied to the surface area during the manufacturing process, the abrasive force of the surface area is maximized, thereby maximizing the efficiency in its use.

While the invention has been shown and described with reference to certain preferred embodiments thereof, it will be understood by those skilled in the art that various changes in form and details may be made therein without departing from the spirit and scope of the invention as defined by the appended claims.

What is claimed is:

1. A callus-removing skin-file, comprising:
    a base plate made of glass;
    an abrasive layer formed on the base plate by sanding; and
    a coating layer coated on the upper surface of the abrasive layer with a mixture of epoxy resin, a hardening agent and emery.

2. The callus-removing skin-file of claim 1, wherein the amount of epoxy resin is 20 to 25 percent by weight, the amount of the hardening agent is 40 to 55 percent by weight and the amount of the emery is 15 to 20 percent by weight.

3. The callus-removing skin-file of claim 1, further comprising a protective layer formed on the back surface of the base plate which prevents the spread of pieces of glass upon the breakage of the base plate.

4. The callus-removing skin-file of claim 1, further comprising a brush formed on the back surface of the base plate which brushes up calluses.

5. The callus-removing skin-file of claim 1, further comprising a handle portion formed on at least one part of the base plate to which various kinds of advertisements are attachable.

6. The callus-removing skin-file of claim 1, further comprising a groove formed on at least one part of the base plate to which a mirror is attachable.

7. A method of manufacturing a callus-removing skin-file comprising the steps of:
    preparing a base plate made from glass material;
    making a mixture by mixing 20 to 25 percent by weight epoxy resin, a 40 to 55 percent by weight hardening agent and 15 to 20 percent by weight emery;
    forming an abrasive layer by sanding a surface of the base plate;
    coating the mixture on the upper surface of the sanded base plate; and
    hardening the base plate coated with the mixture.

8. The method of claim 7, wherein the glass material is one of selected from plate glass, press glass, flat glass, colored glass and specific glass such as water glass, ripple glass, etc.

* * * * *